United States Patent
Seiler et al.

(10) Patent No.: US 6,836,745 B2
(45) Date of Patent: Dec. 28, 2004

(54) METHOD FOR DETERMINING THE POSITION OF A SENSOR ELEMENT

(75) Inventors: Paul G. Seiler, Villigen (CH); Ralph K. Muench, Oberflachs (CH); Stefan R. Kirsch, Lauchringen (DE)

(73) Assignee: Northern Digital Inc., Waterloo (CA)

( * ) Notice: Subject to any disclaimer, the term of this patent is extended or adjusted under 35 U.S.C. 154(b) by 0 days.

(21) Appl. No.: 10/333,828

(22) PCT Filed: Jul. 10, 2001

(86) PCT No.: PCT/CH01/00431
§ 371 (c)(1),
(2), (4) Date: Apr. 14, 2003

(87) PCT Pub. No.: WO02/08793
PCT Pub. Date: Jan. 31, 2002

(65) Prior Publication Data
US 2003/0200052 A1 Oct. 23, 2003

(30) Foreign Application Priority Data
Jul. 26, 2000 (CH) .............................................. 1475/00

(51) Int. Cl.$^7$ .............................................. G01B 15/00
(52) U.S. Cl. ............. 702/150; 324/207.11; 324/207.17; 324/207.15; 702/155; 702/167
(58) Field of Search ........................... 324/320, 207.12, 324/207.17; 702/155, 167, 150

(56) References Cited

U.S. PATENT DOCUMENTS

| 4,881,035 A | * | 11/1989 | Siebold | ........................ 324/320 |
| 4,945,305 A | * | 7/1990 | Blood | ................... 324/207.17 |
| 5,453,686 A | | 9/1995 | Anderson | |
| 5,767,669 A | | 6/1998 | Hansen et al. | ......... 324/207.14 |
| 6,072,320 A | * | 6/2000 | Verkuil | ........................ 324/750 |

FOREIGN PATENT DOCUMENTS

| EP | 0 993 804 | 4/2000 |
| WO | WO 97/36192 | 10/1997 |
| WO | WO 01/33231 | 5/2001 |

OTHER PUBLICATIONS

Birkfellner W. et al., "Calibration of Tracking Systems in a Surgical Environment," IEEE Trans. Med. Imaging, vol. 17(5), pp 737–742, 1998.

* cited by examiner

Primary Examiner—Kamini Shah
(74) Attorney, Agent, or Firm—Fish & Richardson P.C.

(57) ABSTRACT

A method for determining the position of a sensor element which is used to measure a magnetic alternating field emitted by at least one generator unit. The sensor element receives a signal. Interference fields, which are the fields arising due to eddy currents generated in electrically conductive objects, are calculated. The eddy currents are calculated based on the alternating field. The position can be corrected based on the signal received in the sensor element.

10 Claims, 2 Drawing Sheets

METHOD FOR DETERMINING THE POSITION OF A SENSOR ELEMENT

BACKGROUND OF THE INVENTION

The present invention relates to a method as defined in the preamble to claim 1, a use of the method, an apparatus for executing the method and a computer-program product.

In numerous technical and medical procedures, it is critical that the exact position of a certain object be known. Whereas in medicine, the position of individual tissue elements—such as a tumor, which is to be destroyed or limited in growth through irradiation-must be ascertained, the determination of the position for entry into a computer system, for example for "cyberspace" applications, is of less significance. In these applications, a position-detection or position-entry unit is also referred to as a three-dimensional mouse.

The international patent application by the same applicant, WO 97/36192, describes a known apparatus and a known method, respectively, for determining position. According to the known teaching, it is provided to create an alternating field with the aid of a field-generator unit. Depending on the number of degrees of freedom of a sensor element whose position is to be determined, a plurality of alternating fields can be superimposed over one another. A processing and control unit, which controls the field-generator unit, and processes the signals received from the sensor element, ascertains the position and possibly the location of the sensor unit. In this regard, the content of the above-cited publication constitutes an integral component of this description.

It has been shown that, in magnetic field-based positioning, as is used in, for example, the teaching known from WO 97/36192, eddy currents are generated in adjacent, electrically conductive objects. These currents lead to distortions in the original magnetic alternating field, and therefore to systematic errors. This means that, when the position and orientation of sensor elements in the distorted alternating field are ascertained as if no electrically conductive object were present, the obtained values are systematically skewed.

A method for compensating interfering effects caused by conductive objects is known by the name "distortion mapping." This method is described, for example, in an essay titled "Calibration of Tracking Systems in a Surgical Environment" (Birkfellner et al., IEEE Trans Med Imaging, Vol. 17(5), pp. 737–742, 1998). In the known method, the position and orientation of a sensor element are likewise ascertained with the aid of a position-measurement system that employs magnetic field-based positioning. A second position-measurement system, which is insensitive to electrically conductive objects, is provided for compensating interfering effects. The difference between the positions and orientations determined with the two position-measurement systems is then used to correct the position and orientation determined with the aid of the magnetic field-based position-measurement system.

A drawback of the known method, however, is that, to attain high precision, the position and orientation difference must be measured at as many points as possible. To obtain additional points, a costly interpolation method must be used. The very high outlay is illustrated, in particular, by the following example: If a volume of 1 $m^3$ is supposed to be measured, specifically over 10 cm in all three axes and at ten different orientation angles, 10,000 points are obtained. Furthermore, the aforementioned second position-measurement system is necessary.

In another known method for compensating interfering effects, pulsed DC fields generate magnetic fields. Eddy-current effects are compensated by taking magnetic-field measurements after the eddy-current components contained in the measurement signal have decayed. More detailed explanations of the known method can be found in the publications U.S. 5,453,686 and U.S. 5,767,669. It has been seen that the precision of the obtained results is unsatisfactory. In particular, the compensation is incomplete if the decay times of the eddy-current components exceed the pulse time between two DC pulses. While this can be remedied by lengthening the pulse time, such a solution results in an undesired, lower measurement rate. Moreover, the known compensation method cannot be implemented in position-measurement systems that employ magnetic positioning and generate magnetic alternating fields.

BRIEF SUMMARY OF THE INVENTION

It is therefore the object of the present invention to disclose a method that permits an improved determination of the position and/or the location of a sensor element.

This object is accomplished by the actions disclosed in the characterizing portion of claim 1. The additional claims disclose advantageous embodiments of the invention, an application of the method, an apparatus for executing the method and a computer-program product.

With the method according to the invention, it is possible to eliminate the influence of conductive objects, or at least reduce it significantly. This method is also more general and more precise than the known methods. Finally, the geometry-dependent portion of the calculations can be executed in the sense of a system calibration prior to the actual implementation of the position-measurement system.

BRIEF DESCRIPTION OF THE DRAWINGS

The invention is described in detail below by way of examples illustrated in the drawings. These show.

DETAILED DESCRIPTION OF THE INVENTION

Figure 1:
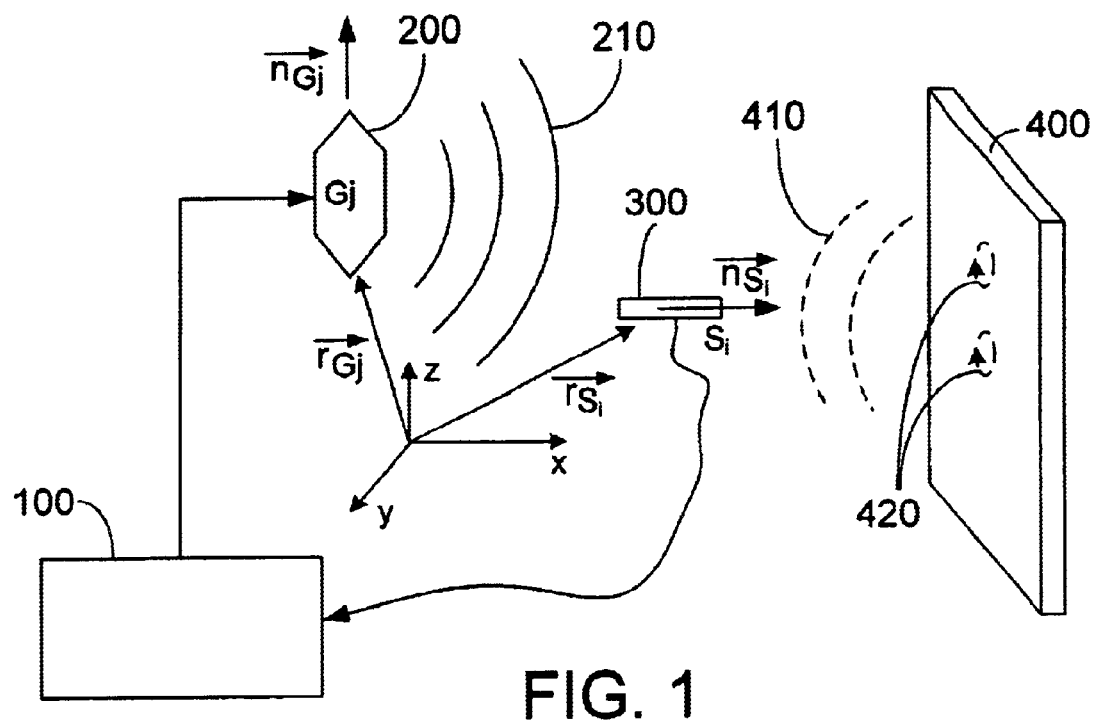
FIG. 1 a schematic representation of a known arrangement, comprising a field-generator unit, a sensor element and a processing and control unit, with an electrically conductive object.

FIG. 1 shows a known arrangement comprising a field-generator unit 200, a sensor element 300 and a processing and control unit 100. The processing and control unit 100 is connected via lines to the field-generator unit 200 on one side and the sensor element 300 on another side. While the field-generator unit 200 is preferably at a known location—meaning that the coordinates x, y, z, including the orientation in the coordinate system, are known—the sensor element 300 can be moved arbitrarily and have any position and orientation. It is noted out here that it is conceivable for the sensor element 300 to be stationary and the field-generator unit 200 to be freely movable; i.e., within the range of the available connecting line to the processing and control unit 100, as is already known from WO 97/36192. It is also entirely plausible for the processing and control unit 100 to be realized in a plurality, of functional units; for example, the control unit for controlling the field-generator unit 200 can be embodied in one functional block, and the processing unit, in which the position of the sensor element 300 is actually calculated, can be embodied in a different functional block. These modifications of the arrangement shown in FIG. 1 do not affect the applicability of the method according to the invention. The same is true for embodiments in which a plurality of field generators is provided at different locations, as is the case in the device according to WO 97/36192, for example.

In the schematic illustration, an electrically conductive object represents the objects that disturb the magnetic positioning of the sensor element 300: Eddy currents 420 are generated in the object 400 and cause the formation of an interference field 410, which is superimposed over the alternating field 210.

Before the method of the invention is described in further detail, general relationships or procedures associated with magnetic field-based positioning are described below.

As already mentioned, in magnetic field-based positioning, also referred to as magnetic positioning, the position and/or the orientation of one or more sensor elements 300 relative to one or more field-generator units 200 is or are determined. The position $\bar{r}_{Si}$ and the orientation $\bar{n}_{Si}$ of the sensor elements $S_i$ can be determined by solving the following equation system, provided that the position $\bar{r}_{Gj}$ and the orientation $\bar{n}_{Gj}$ of the field-generator units $G_j$ are known:

$$F_{ij} = F(\bar{r}_{Si}, \bar{n}_{Si}, \bar{r}_{Gj}, \bar{n}_{Gj}) \quad (1)$$

Here, i is the i-te sensor element and j is the j-te field-generator unit. F is a measurement function of at least one component of the magnetic field, the function being dependent on the magnetic field $\bar{B}(x, y, z, t)$ (e.g., the induced voltage in a sensor coil). Of course, F can also be a function of several sensors combined into one sensor element, which measures all or a plurality of the components simultaneously.

Depending on the type of solution for this equation system, magnetic positioning systems can be divided into two classes:

I. The equation system is inverted; i.e., the sensor-element positions can be calculated from the measured magnetic fields:

$$\bar{r}_{Si} = f_r(F_{ij}) \text{ and } \bar{n}_{Si} = f_n(F_{ij}) \quad (2)$$

Because it is possible to invert the equation system only in very special cases, approximation can be used to bring the field equations into an invertible form.

II. The equation system is solved through optimization; i.e., the sensor-element positions are varied until the values $F_{ij}$ calculated with Equation 1 match the best with the measured values $F_{ij}^M$. One possible method would be a Chi$^2$-Fit according to Levenberg-Marquardt. In this case, the sensor positions $\bar{r}_{Si}$, and $\bar{n}_{Si}$ are varied until $$Chi^2(\bar{r}_{S_i}, \bar{n}_{S_i}) = \sum_j \frac{(F_{ij} - F_{ij}^M)^2}{(\Delta F_{ij}^M)^2} \quad (3)$$

is minimized. For additional information on the Levenberg-Marquardt method, refer to the publication titled "Numerical Recipes in C"(W. H. Press, S. A. Teukolsky, W. T. Vetterling and B. P. Flannery; Cambridge University Press, 1994). It is also possible to combine the two solution approaches.

Because the variable $F_{ij}$ measured by the sensor element $S_i$ is only a function of the relative position of the sensor element $S_i$ and the field-generator unit $G_j$, the roles of sensor element and field-generator unit are interchangeable in all magnetic position-measurement systems.

If temporally varying magnetic fields are used, they generate eddy currents 420 in adjacent, electrically conductive objects 400, as mentioned above. These eddy currents lead to distortions in the original magnetic alternating field 210 and thus to systematic errors in determining the position. This means that, when the position and orientation of sensor elements are determined in the distorted alternating field as if no electrically conductive object 400 were present, the obtained values are systematically skewed.

So that the method of magnetic positioning can also be used in the vicinity of electrically conductive objects 400 without being affected by errors caused by these objects, the alternating-field distortions and their influence on the determination of sensor-element position and sensor-element orientation are determined according to the invention. Hence, the systematic errors that do occur can be corrected, which can considerably improve the precision of the position and/or the orientation.

With a known measurement device, it has been shown that a measurement error of 4 cm could be reduced to less than 1.5 mm with the method according to the invention.

These corrections can basically also be found using the technique of finite elements and electrodynamics equations. The preferred embodiment of the method according to the invention is further distinguished from the method of finite elements by the fact that a substantial reduction in the position calculation was achieved because much of the calculating can take place in advance, for the purpose of system calibration.

The method according to the invention is described below. For the sake of simplicity, it is assumed that-the object 400 comprises an electrically conductive plate; i.e., a flat, limited surface. The method according to the invention is likewise applicable to objects 400 possessing a relevant expansion (depth) that extends in the direction of an imaginary line from the field-generator unit 200 to the object 400. For this purpose, the side facing the field-generator unit 200 is approximated by a multi-surface structure. This is permissible because the eddy currents 420 only slightly penetrate the surface. The depth of a three-dimensional object 400 is therefore irrelevant. In the mathematical determination of the interference field 410, therefore, the object 400 is approximated by a multi-surface structure in the manner described above.

The following discussion focuses on considerations pertaining to the calculation of field distortions with a conductive plate. The results obtained from the calculation can be obtained analogously to those for more general object shapes.

If an electrically conductive object 400 is located in a magnetic field $\bar{B}_0(x,y,z,t)$ that changes over time, eddy currents 410 (FIG. 1) are induced into the surface of the object 400. These eddy currents 410 create an additional magnetic field $\bar{B}'(x,y,z,t)$, which is superimposed over the original field $\bar{B}_0(x,y,z,t)$ and results in the field $\bar{B}_{Res}(x,y,z,t)$. $\bar{B}_{Res}(x,y,z,t)$ is distorted with respect to the field $\bar{B}_0(x,y,z,t)$. For this distorted field to be calculated, the induced alternating field $\bar{B}'(x,y,z,t)$ must be known. A field $\bar{B}_1(x,y,z,t)$, which adequately describes $\bar{B}'(x,y,z,t)$, can be calculated from the Biot-Savart law of electrodynamics (Equation 4) if the local and temporal course of the eddy currents 410 in the object 400 in N different, dot-shaped current elements is known:

$$B_1(\vec{P}_R, t) = \sum_{i=0}^{N} \frac{\mu_0 \mu_r I_i(t) \Delta \vec{s}(t) \times \vec{r}}{4\pi \, r^3} \quad (4)$$

where $\vec{P}_R=(x,y,z)$ represents a point in space and the vector $\vec{r}$ points from the current element to the point $\vec{P}_R$. If necessary, pre-factors can be incorporated into and/or contained in the amount of the factor $\vec{\Delta s}(t)$. A detailed calculation of $\overline{B}_1(x,y,z,t)$ is possible through the introduction of longitudinal or surface currents, etc., instead of dot currents. This would, however, alter the notation of Equation 4. In most instances, in contrast, Equation 4 can be adopted as it appears above, provided that N is selected to be large enough.

The field distortions are therefore calculated in two steps. The first step is the determination of the eddy currents 410, and the second step is the calculation of an interference field $\overline{B}_1(x,y,z,t)$ that has been generated by the eddy currents 410 and adequately describes the interference field $\overline{B}'(x,y,z,t)$.

Figure 2:
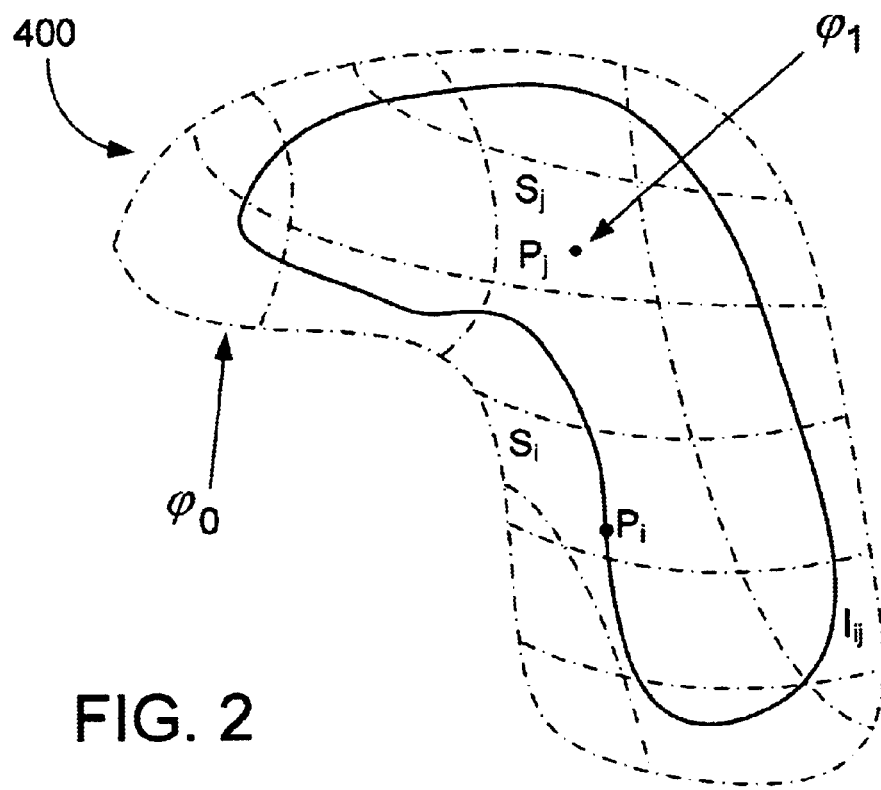
FIG. 2 an electrically conductive object.

FIG. 2 shows the object 400, which is divided into a multi-surface structure comprising an arbitrary number of segments, for determining the interference field 410. With this division and various other assumptions, first the eddy currents are calculated.

The eddy currents flow at the surface of the object 400 with a penetration depth that is "insignificant" for the theory. For calculating the aforementioned interference field $\overline{B}'(x,y,z,t)$ precisely enough, it suffices to know the temporal current course at a few points on the surface of the object 400. The number of points depends on the required level of precision. The eddy currents are therefore calculated in points that lie on or near the surface of the object.

In a first step, the object is subdivided into N arbitrarily shaped segments, which advantageously (but not necessarily) cover the entire object. The segments are then uniquely identified with $S_i\{0 \leq i \leq N-1\}$, with i being used as the index.

In a second step, an interpolation node $P_i$ is selected for each segment. It is advisable, but not compulsory, to define the same number of interpolation nodes as segments and allocate them uniquely to the segments. For the sake of simplicity, it is assumed below that N segments $S_j$, each having a uniquely allocated interpolation node $P_i$, are defined. The current density $\vec{i}_i(t)$ in the interpolation node $P_i$ of each segment $S_i$ is calculated with the following formula:

$$\vec{i}_i(t) = \sum_{j=0}^{N} \vec{i}'_{ij}(t) \text{ with } j <> i \quad (5)$$

where $\vec{i}'_{ij}(t)$ is the current density of the eddy current $I_{ij}(t)$, which is caused by the change in flux of the field of $\overline{B}_0(x,y,z,t)$ in the segment $S_j$, and flows through the interpolation node $P_i$ or in the area surrounding the interpolation node $P_i$. The calculation of the individual eddy currents $I_{ij}(t)$ is described in the next paragraph. The following applies:

$$\vec{i}'_{ij}(t) = \frac{\vec{\lambda} I_{ij}(t)}{A_3} \quad (5a)$$

where $\vec{\lambda}$ is a directional vector (or a nearly collinear direction thereto) of the current flow through the interpolation node $P_i$ in the interpolation node $P_j$, and, with $A_3$, is the cross-sectional surface of the flow line, where:

$$A_3 = \pi \cdot r^2(h) \quad (5b)$$

and where
r=radius of the circular cross-sectional surface; and
h=penetration depth.

If the current densities $\vec{i}_i(t)$ are known, $\overline{B}_1(x,y,z,t)$ can be calculated as the interference field caused by $\overline{B}_0(x,y,z,t)$. For this purpose, $\vec{i}_i(t) \cdot A(S_i)$ can be inserted directly into Equation 4, where $A(Si)$ is the surface area of the segment $S_i$. $\overline{B}_1(x,y,z,t)$ can be regarded as $\overline{B}'(x,y,z,t)$ in most cases. As a second-order effect, $\overline{B}_1(x,y,z,t)$ can be inserted as an original field at this point in order to re-calculate eddy currents for a second interference field $\overline{B}_2(x, y, z,t)$ (mutual influence of the eddy currents) that is superimposed with $\overline{B}_0(x,y,z,t)$ and $\overline{B}_1(x,y,z,t)$. In a second approximation, $\overline{B}'(x,y,z,t)$ would be equal to the sum of $\overline{B}_1(x,y,z,t)$ and $\overline{B}_2(x,y,z,t)$. This iterative procedure can be continued for effects of any order. The first-order effect is sufficient in most applications, however.

An individual eddy current $I_{ij}(t)$ is a current flow that flows through the interpolation node $P_i$ and is caused by the change over time in the field flux through the interpolation node $P_j$. The inductance $L_{ij}$, its ohmic resistance $R_{ij}$ and the change in flux over time $$\frac{d\Phi_j}{dt}$$

are necessary for calculating $I_{ij}(t)$. If these variables are known, $I_{ij}(t)$ is given by the solution of the differential equation $$\frac{d\Phi_j}{dt} - L_{ij}\frac{dI_{ij}(t)}{dt} - R_{ij}I_{ij}(t) = 0 \quad (6)$$

In many cases, $\overline{B}_0(x,y,z,t)$, may be periodic, or even oscillate harmonically, but this is not necessary for the validity of the method according to the invention.

The inductance $L_{ij}$ and the ohmic resistance $R_{ij}$ are indicated by the geometric shape of the eddy current $I_{ij}(t)$, and the change in flux $$\frac{d\Phi_j}{dt}$$

is indicated by the field $\overline{B}_0(x,y,z,t)$ at the location $P_j$, along with the surface area of the segment $S_j$. In the following steps, first the shape of the eddy current is described; from this, the inductance $L_{ij}$ and the ohmic resistance $R_{ij}$ are calculated.

Hypothetically, a single magnetic-field line B passes through a small surface dA around a point P on the object. In this case, the induced current flows would be circular in the vicinity of the point P, and at the edge of the object 400 they would follow the periphery; i.e., they would assume the outer shape of the object. The shape of any eddy current is a current along a level line of a surface that fulfills the potential equation $$\Delta \varphi = \frac{\partial^2 \varphi}{\partial x^2} + \frac{\partial^2 \varphi}{\partial y^2} = 0 \quad (7)$$

where $\varphi(x, y)$ represents the potential. The marginal conditions of the unique solution to Equation 7(determined from φ(x, y)) can be seen in FIG. 2 (namely, $\phi_0$ at the edge of the object and $\phi_1$ in the point $P_j$, $\phi_0 <> \phi_1$). This potential equation is best solved numerically. With the shape of the eddy current and the penetration depth h of the current into the material, the single current flow can be considered as a conductor loop having an annular material cross-section and the diameter of the penetration depth (other practical material cross-sectional geometries are conceivable, of course, but do not change the calculations significantly).

The ohmic resistance of the conductor loop is therefore $$R = \frac{l\rho}{\left(\frac{h}{2}\right)^2 \pi} \quad (8)$$

where

R=ohmic resistance [Ω]

l=length of conductor loop [m]

h=penetration depth of current [m]

ρ=specific electrical resistance of the material [Ωm]

The inductance of the conductor loop is given by $$L = \frac{2W}{i^2} \quad (9)$$

and can be numerically calculated, where $$W = \int_{space} \frac{\vec{B}^2}{2\mu_0} dV \quad (10)$$

signifies the stored energy in the magnetic field generated in the conductor, if a current i flows in the conductor. There are many other "random" approximation formulas that can replace Equations (8), (9) and (10), and produce similar results.

The following applies for calculating the flux $\Phi_j(t)$ from the field $\overline{B}_0(x,y,z,t)$:

$$\Phi_j(t) = \overline{B}_0(x, y, z, t) \cdot \vec{A}_j \quad (11)$$

where $\overline{B}_0(x,y,z,t)$ represents the undisturbed field at the point $P_j$, and $\vec{A}_j$ represents the surface normal of the segment $S_j$, including the amount of the surface area of the relevant segment. Formula 11 is an approximation formula for the generally valid formula $$\Phi_j(t) = \int_{A_j} \vec{B}_0(x, y, z, t) d\vec{A} \quad (11a)$$

and may be applied when B over $A_j$ is sufficiently homogeneous (for example, for small surface areas $A_j$). At this point, it should be mentioned that the surface area $A_j$ of the segment $S_j$ does not always lie completely inside the conductor loop $I_{ij}(t)$. Corrections could be made in this regard, but generally they are not necessary.

The fairly intensive calculation of the inductances $L_{ij}$ and the ohmic resistances $R_{ij}$ can be made in advance with Formulas (8), (9) and (10) because they alone depend on the geometry and material of the object, for the purpose of system calibration. Formulas (4) and (5) can be used and solved to calculate $\overline{B}_1(x,y,z,t)$ at a different time, particularly when the excitation field $\overline{B}_0(x,y,z,t)$ is known. Iterations such as the use of the field $\overline{B}_1(x,y,z,t)$ to calculate a field $B_2(x,y,z,t)$, etc. are possible. Such iterations could also be done in advance; for example, they can be inserted into the inductances $L_{ij}$. This is not practical, however, unless regular corrections of a higher order are required.

In practice, magnetic positioning involves determining the location and orientation of one or more sensor elements 300 (FIG. 1) in a magnetic field generated by one or more field-generator units 200. In the coordinate system used, the position of the field-generator unit(s) 200 is known. In the case of magnetic alternating fields, adjacent, electrically conductive objects 400 create field distortions due to eddy currents 420 induced in the objects 400. The method according to the invention for correcting these distortions, whose theoretical principles are outlined above, is implemented as follows The location of the electrically conductive objects 400 in the aforementioned coordinate system is known, or is determined through measurement. The object coordinates are entered into a computer program, which is used to calculate the eddy currents 420 and the resulting field distortions, such that the location coordinates used in the above formulas are defined in the coordinate system defined by the field-generator unit 200. With the computer program, the interference field generated by the eddy currents 420 is calculated. Taking into account the eddy currents 420, the Equation system 1 changes as follows:

$$F_{ij} = F(\vec{r}_{S_i}, \vec{n}_{S_i}, \vec{r}_{G_j}, \vec{n}_{G_j}) + \sum_{k=1}^{P} F'_k(\vec{r}_{S_i}, \vec{n}_{S_i}, \vec{r}_{G_j}, \vec{n}_{G_j}) \quad (12)$$

where $F'_{ij}$ represents the interference caused by the eddy currents 420 of the object k. P is the number of objects. The type of magnetic position-measuring system determines how this correction is implemented.

I. In systems based on Equation 2, the measured values are corrected iteratively; i.e., the undisturbed solution according to Equation 2 is calculated first. The correction term F' can be calculated with the found position of the sensor element 300, and derived from the measurements $F_{ij}^M$. A position is re-calculated with the corrected measurements. This algorithm is continued until the variation in the calculated positions is below specified tolerance thresholds.

II. In systems based on Equation 3, the solution algorithm need not be changed. In the Chi² sum, the magnetic field with eddy-current corrections from Equation 12 is used instead of the model for calculating the magnetic field $F_{ij}$ according to Equation 1, which is free from eddy currents.

III. With certain prerequisite conditions, it may also be possible to invert the equation system 12, which leads to a solution corresponding to Equation 2.

Figure 3:
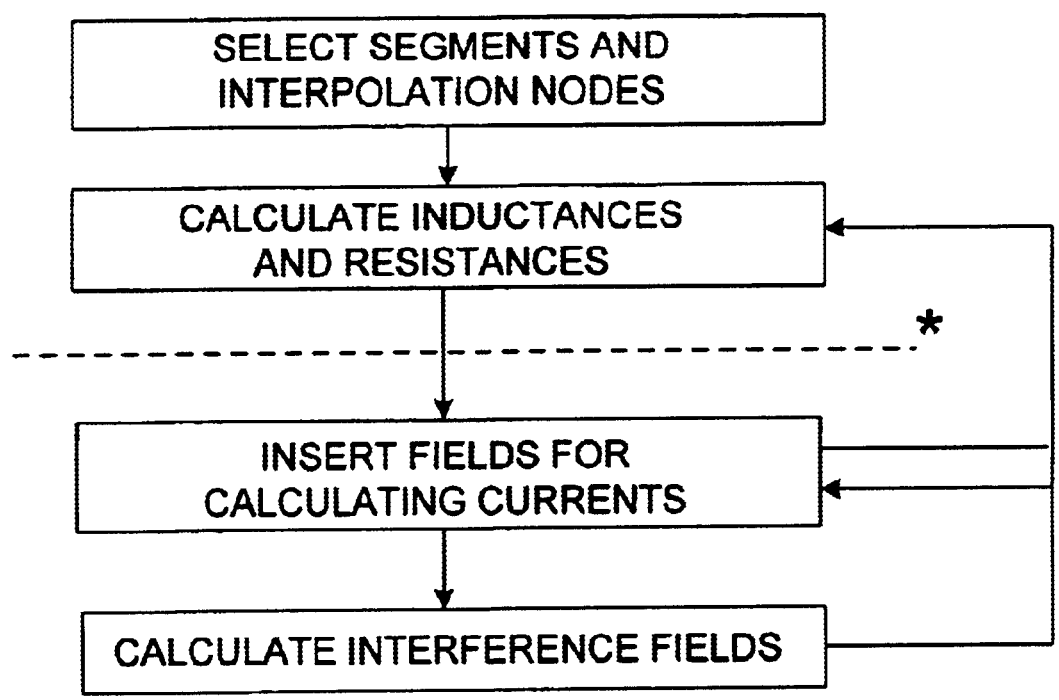
FIG. 3 a flow diagram showing a few method steps of the method according to the invention.

FIG. 3 is a simplified representation of a structogram of a computer program that operates in accordance with the method of the invention. The individual processing steps were already explained in detail in conjunction with FIGS. 1 and 2.

In particular, the method according to the invention can also be employed for objects with openings (holes), in which case the number L of openings may be arbitrary. For the above-described solution method, first the marginal condition of the potential equation (7) at the edges of the openings must be equal to the potential $\phi_0$ at the edge of the object. Furthermore, N times L (N=number of interpolation nodes; L=number of openings) current flows $I_{ik}$ are included, and are added into the sum (5) (k wanders from 1 to L).

The additional eddy-current flows $l_{ik}$ can be calculated individually, analogously to the eddy-current flows $I_{ij}$, that is, by solving the potential equation (7) for the shape of the current and calculating the inductance and the resistance according to Equations (8) and (9). In the potential equation (7), it must be kept in mind, however, that the marginal condition is not "$\phi_1$ in point Pj," but "$\phi_1$ at the edge of the opening k." If the openings are large, Formula 11a may be used in place of the approximation formula 11 for calculating the flux.

Individual conductor loops can also be calculated with this method, because the aforementioned openings -can be expanded as close as desired to the periphery of the objects to be calculated. The simplest example is a circular ring, which may be viewed as a disk having an opening that is nearly the same size. In this example, the current flows $I_{ij}$ are negligible (the interpolation nodes could be omitted), and there is only one $I_{ik}$, whose shape is defined by the circular ring. If the interpolation nodes are omitted, the field $B_1$ should be determined by the line integral with Equation 4.

An additional consideration is that it is possible to shield against interfering influences by unknown objects by providing a conductive plate between the field-generator unit and the object, with the size, shape and position of the plate being known. Thus, while the field distortions of this plate must be taken into account, all other electrically conductive objects located on the other side of the plate, with respect to the field-generator unit, can continue to be disregarded because of the shield.

What is claimed is:

1. A method for determining the position of a sensor element, which is used to measure a magnetic alternating field emitted by at least one generator unit, the method comprising: receiving a signal in the sensor element, wherein calculating, in a first approximation, interference fields, the fields arising due to eddy currents generated in electrically conductive objects, and calculating the eddy currents in the object based on the alternating field, and calculating the interference fields, based on the calculated eddy currents, and correcting the position that can be determined based on the signal received in the sensor element.

2. The method according to claim 1, wherein, to further improve the determination of position, at least one additional iteration is performed, comprising calculating additional eddy currents in the object based on calculated interference fields, and calculating additional interference fields based on the additional eddy currents.

3. The method according to claim 1 comprising determining the position and shape of the objects, and calculating resistances in the object according to the equation $$R = \frac{l\rho}{\left(\frac{h}{2}\right)^2 \pi}$$

and calculating inductances in the object according to the equation $$L = \frac{2W}{i^2}.$$

4. The method according to claim 3, comprising performing an additional iteration to further improve the inductances comprising calculating additional eddy currents in the object, based on calculated interference fields, and determining additional inductances, based on the additional eddy currents.

5. The method according to claim 3, wherein the determination of the objects and the determination of the resistances and inductances in the object take place in advance for the purpose of system calibration; i.e., prior to the calculations that take into account the alternating field.

6. The method according to claim 1, wherein the following procedure is followed for determining the eddy currents:

the objects are divided into segments ($S_i$) and interpolation nodes ($P_i$);

the current density ($i_i$) in the interpolation nodes ($P_i$) is determined; and the current densities ($i_i$) are determined from the eddy currents ($I_{ij}$).

7. A use of the method according to any one of claims 1 through 6 for magnetic field-oriented positioning in "cyberspace" applications.

8. An apparatus for executing the method according to any one of claims 1 through 6, wherein at least one field-generator unit, at least one sensor element and a processing and control unit are provided, with the field-generator unit and the sensor element being connected to the processing and control unit.

9. The apparatus according to claim 8, wherein at least one electrically conductive object is provided for shielding the field-generator unit.

10. A computer-program product that can be loaded into the internal memory of a digital computer and contains software code segments, with which any one of the methods according to claims 1 through 5 can be executed when the product is running on a computer.

* * * * *